(12) United States Patent
Cassidy et al.

(10) Patent No.: US 6,831,746 B2
(45) Date of Patent: Dec. 14, 2004

(54) SYSTEM, METHOD, AND APPARATUS FOR NON-INTRUSIVELY DETERMINING CONCENTRATION OF A SOLUTE IN A SOLUTION

(75) Inventors: Christopher S. Cassidy, Stillwater, OK (US); Kenneth H. Church, Stillwater, OK (US); William Ardrey, Cleveland, OK (US); Keith Teague, Stillwater, OK (US)

(73) Assignee: Sciperio, Inc., Stillwater, OK (US)

( * ) Notice: Subject to any disclaimer, the term of this patent is extended or adjusted under 35 U.S.C. 154(b) by 0 days.

(21) Appl. No.: 10/161,079

(22) Filed: May 30, 2002

(65) Prior Publication Data

US 2003/0107012 A1 Jun. 12, 2003

Related U.S. Application Data

(60) Provisional application No. 60/293,976, filed on May 30, 2001.

(51) Int. Cl.[7] .............................................. G01N 21/61
(52) U.S. Cl. ...................... 356/437; 356/367; 250/373; 600/322
(58) Field of Search ................................ 356/432–442, 356/246, 300, 39–42; 250/372–373; 600/310–323, 473, 476; 128/633, 665

(56) References Cited

U.S. PATENT DOCUMENTS

| | | | | |
|---|---|---|---|---|
| 4,324,131 A | * | 4/1982 | Rosencwaig | 73/61.58 |
| 5,214,288 A | * | 5/1993 | Oka et al. | 250/373 |
| 5,416,579 A | * | 5/1995 | Barshad et al. | 356/300 |
| 5,477,327 A | * | 12/1995 | Bergman | 356/367 |
| 5,601,079 A | * | 2/1997 | Wong et al. | 600/322 |
| 5,680,209 A | * | 10/1997 | Machler | 356/319 |
| 6,130,439 A | | 10/2000 | Le Menn | |
| 6,166,807 A | * | 12/2000 | Kawamura et al. | 356/364 |
| 6,526,309 B1 | * | 2/2003 | Chance | 600/473 |
| 6,640,116 B2 | * | 10/2003 | Diab | 600/322 |

FOREIGN PATENT DOCUMENTS

| | | | |
|---|---|---|---|
| EP | 000039088 A1 | * | 11/1981 |
| JP | 360170742 A | * | 9/1985 |
| JP | 402130458 A | * | 5/1990 |

OTHER PUBLICATIONS

International Search Report, Application No. PCT/US02/17361, dated Sep. 23, 2002.

Article entitled Flow–Injection Chemiluminescence Sensor for the Determination of Free Chlorine in Tap Water, by Qin et al., published in *Analytical Letters*, 30(1), 11–19 (1997).

Article entitled "Water–core waveguide for pullution measurements in the deep ultraviolet", by Dress et al., published in *Applied Optics*, Jul. 20, 1998, vol. 37, No. 21, pp 4991–4997.

* cited by examiner

*Primary Examiner*—Gregory J. Toatley, Jr.
*Assistant Examiner*—Sang H. Nguyen
(74) *Attorney, Agent, or Firm*—Needle & Rosenberg, PC.

(57) ABSTRACT

Concentration of a solute in a solution is determined. Light from a light source is received at a chamber containing the solute and the solution. The light is transmitted along an optical path length of the chamber, through the solute and the solution, and output from the chamber. The light output from the chamber is detected by a detector. The optical path length of the chamber is selected to optimize sensitivity of the detector. The concentration of the solute in the solution is determined based on the light received by the detector.

58 Claims, 3 Drawing Sheets

SYSTEM, METHOD, AND APPARATUS FOR NON-INTRUSIVELY DETERMINING CONCENTRATION OF A SOLUTE IN A SOLUTION

CROSS REFERENCE TO RELATED APPLICATIONS

This application claims the benefit of U.S. Provisional Application No. 60/293,976 filed May 30, 2001.

Portions of this invention were made with Government support (Contract Nos. 0CAST 5662 and 5833). The Government may have certain rights in this invention.

BACKGROUND

The present invention is directed to a system, method, and apparatus for determining concentration of a solute in a solution. In particular, the present invention is directed to a system, method, and apparatus for determining concentration of a solute in a solution in a non-intrusive manner.

It is often desirable to be able to determine the concentration of a solute in a solution. For example, it is desirable to be able to determine the concentration of chlorine in treated water.

Active chlorine content of treated water is typically 1–10 ppm, and nominally levels are less than 5 ppm. However, those levels may rise as high as 10 ppm during shock treatments.

Conventional commercial chlorine detectors have many drawbacks. For example, they do not produce results in real time and often require human intervention to make interpretations based on color matching. Also, they typically employ a reagent that contaminates water supplies. Furthermore, they lack support electronics to control chemical feed and/or water quality control.

Most substances absorb radiation in the UV/VIS/NIR (Ultra Violet/Visible/Near Infrared) regions of the electromagnetic spectrum. Each chemical species allows a specific amount of light of a given wavelength to be transmitted, thus creating a "signature" for that species due to the wavelength-dependent index of refraction. By strategically picking off peaks in absorption (attenuation of a particular wavelength band), it is possible to classify and even quantify various chemical species.

Theories have been posited for utilizing absorption spectra in the UV region to detect concentration of a solvent in a solution. For example, "Water-core waveguide for pollution measurement in the deep ultraviolet", by Peter Dress et al. describes evaluation of the performance of UV fibers and their degradation over time due to excessive exposure. There is a significant absorption peak for active chlorine centered at 290 nm for a pH of 10.2, as observed in Dress et al. This peak can shift in wavelength depending on pH of the water sample. With decreasing pH, the absorption peak shifts to lower wavelengths or higher energies, while the opposite effect is observed with increasing pH. While Dress et al. suggests use of absorption spectra to detect chlorine concentration, this paper presents data showing poor results below 10 ppm.

In "Flow-injection chemiluminescence sensor for the determination of free chlorine in tap water", by Wei Qin et al., chemiluminescence is explained. One of the drawbacks of the method described in Qin et al. is that it requires an injection of the reagent luminol. Also, Qin et al. reports a lack of sensitivity required for low concentration measurement.

There is thus a need for a non-invasive and non-destructive technique for determining low level concentrations of a solute in a solution.

SUMMARY

It is therefore an object of the present invention to provide a system, method, and apparatus for detecting concentration of a solute in a solution in a non-invasive, non-destructive manner.

According to exemplary embodiment, this and other objects are met by a system, method, and apparatus for determining concentration of a solute in a solution. Light from a light source is received at a chamber containing the solute and the solution. The light is transmitted along an optical path length of the chamber, through the solute and the solution, and output from the chamber. The light output from the chamber is detected by a detector. The optical path length of the chamber is selected to optimize sensitivity of the detector. The concentration of the solute in the solution is determined based on the light received by the detector.

The objects, advantages and features of the present invention will become more apparent when reference is made to the following description taken in conjunction with the accompanying drawings.

DETAILED DESCRIPTION

Figure 1A:
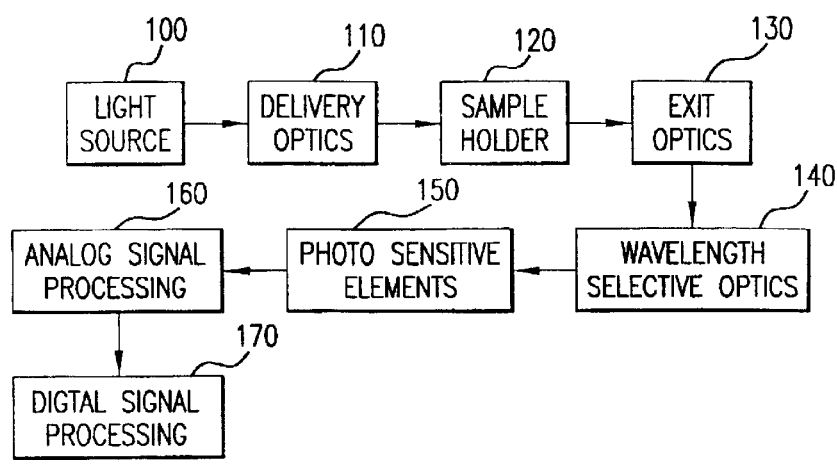
FIG. 1A illustrates an exemplary system for detecting the concentration of a solute in a solution.

According to an exemplary embodiment, a non-invasive, non-destructive approach has been developed for detecting low level concentration of a solute in a solution. An exemplary system for concentration detection is shown in FIG. 1A.

The system includes a sample chamber 120 that contains the solute, such as chlorine, mixed with a solvent, such as water, in a solution. The chamber 120 may be a pipe or tube that may be adjusted in length to adjust the optical path length. The pipe or tube may also be adjusted in diameter to allow more water to flow into the pipe as well as to provide a larger cross sectional area.

Light from a light source is delivered to the sample chamber 120 via delivery optics 110. The light is transmitted through the solution in the chamber and delivered via exit optics 130 to a detector. The detector includes wavelength selective optics 140 and photosensitive elements 150. The wavelength selective optics 140 filter out wavelengths of light, including the peak absorption wavelengths for the solute, and the photosensitive elements detect the intensity of detected light at those wavelengths. The wavelength selective optics may include, e.g., a diffraction grating or filters, and the photosensitive elements may include, e.g., photosensitive diodes. The detected intensity is fed to an analyzer that includes analog signal processing 160 and digital signal processing 170.

Figure 1B:
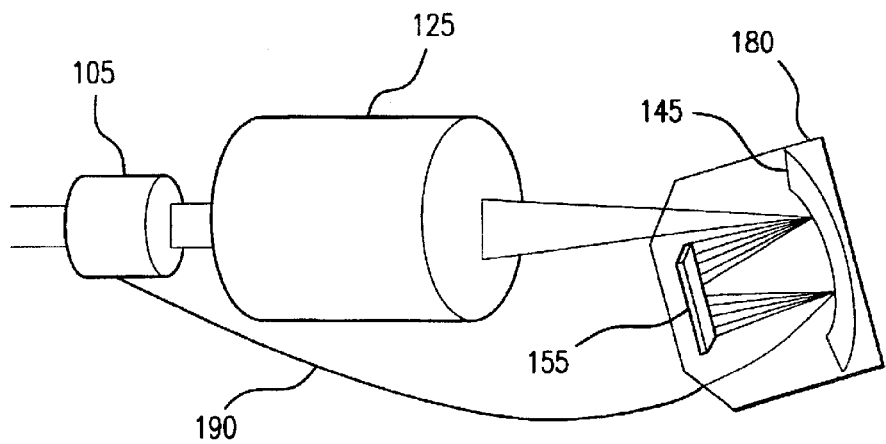
FIG. 1B illustrates an exemplary implementation of elements of the system shown in FIG. 1A.
Figure 2:
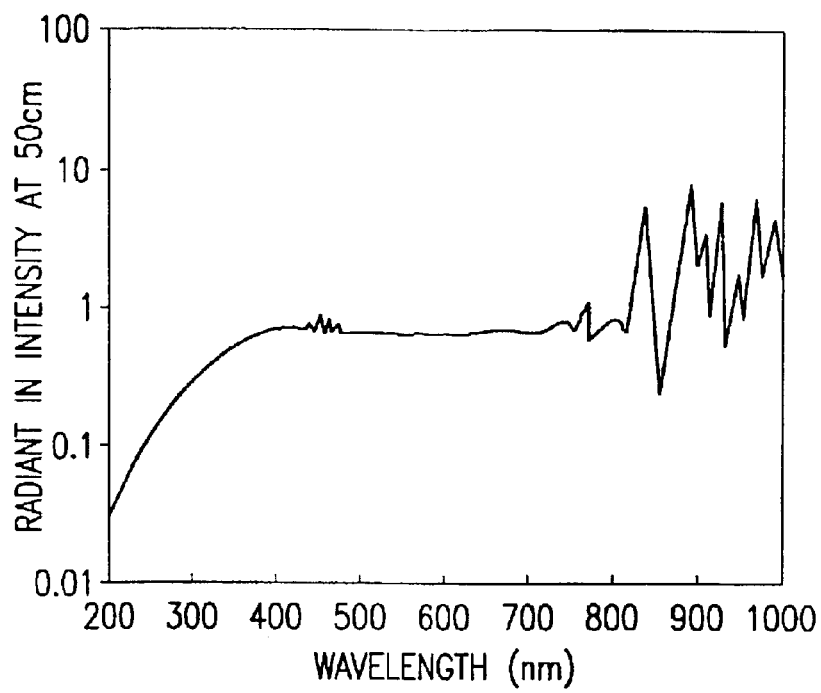
FIG. 2 illustrates an exemplary spectral distribution of a light source.

FIG. 1B illustrates in detail an example of implementation of elements of the detection system shown in FIG. 1A. According to an exemplary embodiment, the input light from the light source is broadband. The wavelength band may change, depending on the absorption characteristics of the solute. For example, for chlorine concentration detection, a flashed xenon arc lamp 105 may be used as the light source to generate radiation in the UV spectral region of interest. The xenon source contains some intensity of all wavelengths over the range from 190 nm to 3000 nm. Its spectral distribution is displayed in FIG. 2. The ability to selectively pulse the lamp allows for greater flexibility when selecting integration times for the detector.

The sample chamber 125 may be cylindrical and may be constructed of polyvinyl chloride (PVC) tubing with fused-silica windows. Water may be passed through tubes attached to either end of the cylindrical chamber. The diameter of the tube may be chosen to match the size of the optic used to focus the output light onto the input slit of the detector, e.g., spectrograph.

According to one embodiment, the detector 180 includes a 256-element detector array 155 and a diffraction grating 145. The detector may be coupled to a parallel spectrograph that allows for simultaneous acquisition of reference and source signals. Light may be coupled into an UV-enhanced fused-silica fiber 190 directly from the light source and fed into the spectrograph for use as a reference. As depicted in FIG. 1B, half of the detector elements are dedicated to the reference signal and half to the source signal. The simultaneous sampling of source and reference signals make possible the elimination of noise contributed by fluctuations in the light source.

Although not shown in FIG. 1B, a driver/amplifier may be used as the analyzer. The driver/amplifier may be custom built or an off-the-shelf C4070 driver/amplifier. The driver/amplifier may be a combination video signal processor and control signal generator for the detector array. The reading of the detector may be similar to the method used with most Photodiode Arrays (PDA's) or Charge Coupled Devices (CCD's).

The C4070 performs a current integration on the video output of the detector and generates a digital signal that is used to trigger data acquisition. An analog-to-digital card, e.g., either a custom built card or an off-the-shelf PC-based data acquisition card, receives the trigger signal and buffers a series of data points. PC software may be used to plot the data on a computer screen for evaluation and save it to an ASCII text file for later processing. A DSP-based micro controller may be used to regulate the integration time (with respect to the detector integration time referenced to the length of exposure) and control the flashing of the lamp.

The delivery optics and exit optics are not shown in FIG. 1B, in the interest of simplifying the illustration. It will be appreciated that these optics may be implemented in any conventional manner.

Figure 3:
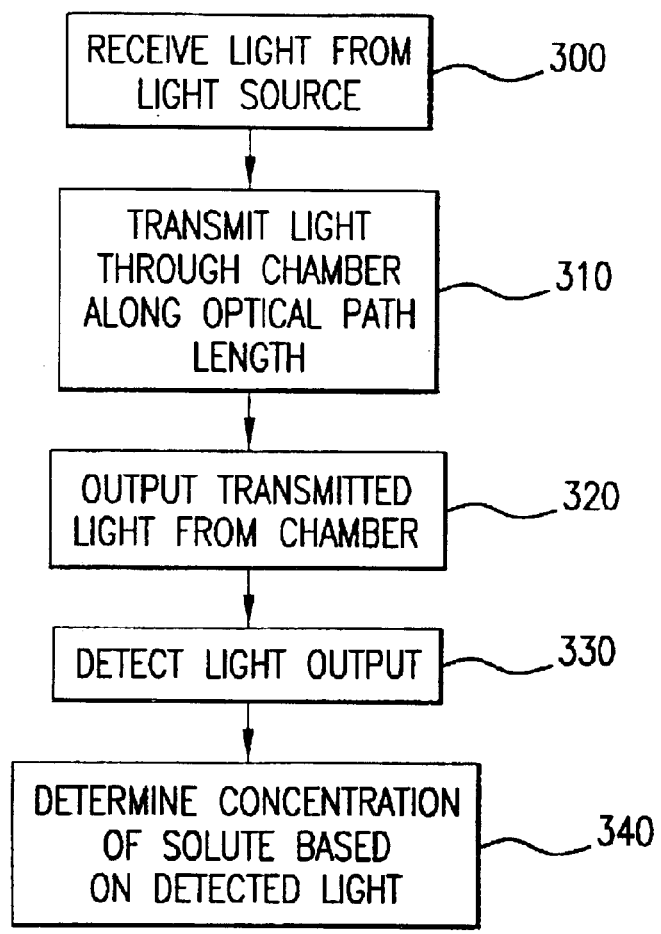
FIG. 3 illustrates an exemplary method for detecting solute concentration according to an exemplary embodiment.

FIG. 3 illustrates an exemplary method for determining concentration of solute in a solution. The method begins at step 300 at which light supplied by a light source is received at the chamber containing the solute and the solution. At step 310, the received light is transmitted along the optical path length of the chamber, through the solute and the solution. At step 320, the transmitted light is output from the chamber. At step 330, the light output from the chamber is detected by the detector at a sensitive determined by the optical path length. At step 340, the concentration of the solute is determined based on the detected light.

Referring again to FIGS. 1A and 1B, the optical path length of the chamber 120 affects the sensitivity of the detector 180. For a given intensity and molar absortivity of solute, e.g., chlorine, the optical path length determines the measurement range for the detector. As the optical path length of the chamber gets longer, the measurement range shrinks, and the resolution of the detector goes up. If the optical path length gets shorter, then the measurement range increases, and the resolution becomes more course.

The amount of chlorine in water or the molar concentration may vary from water supply to water supply. Drinking water may have concentrations on the order of parts per million (ppm). Therefore, detection of a few parts per million is the necessary low end sensitivity level for the detector for detection of chlorine concentration.

The relationship between the optical path length of the chamber and the detector sensitivity may be represented by a generalized set of equations. These equations may be derived by relating the signal to noise ratio (SNR) of the detector type used to losses in the measurement media.

For two measurement wavelengths $\lambda_{ref}$ and $\lambda_{sig}$, where $\lambda_{ref}$ is a wavelength unaffected by the solute, and $\lambda_{sig}$ is the peak absorption wavelength of the solute, then a set of equations may be developed that depend only on optical path length and solute concentration for a given species. Also, given absorption coefficients $\alpha$ for any solvent and solute, it is possible to develop a set of generalized equations with the same dependencies.

To simplify the derivation, the following assumptions are made:

1) The SNR is 10000:1 for photodiodes.
2) The light source has the same intensity at both measurement wavelengths
3) Light only passes through air and water. No optics are considered here, since the optics only add an integer loss.
4) The incident light intensity is high enough that with loss to water the reference intensity is large enough to saturate the detector.

Figure 4A:
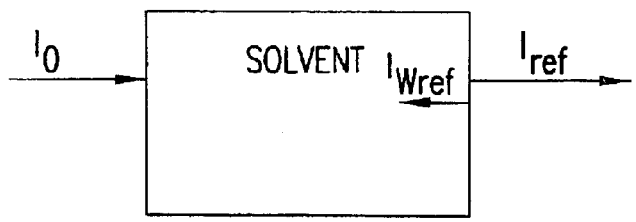
FIGS. 4A and 4B illustrate exemplary paths taken by incident light through a chamber containing a solute in a solution.
Figure 4B:
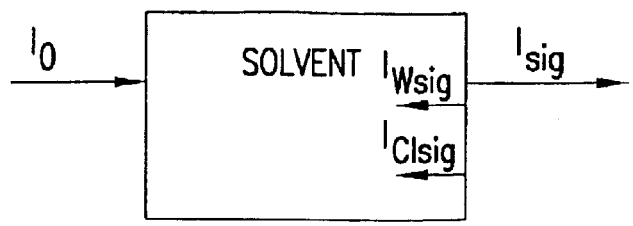

To help understand the relationship between loss and sensitivity, FIGS. 4A and 4B illustrate the paths taken by incident light through a solvent in a chamber at the reference and signal wavelengths, respectively.

From FIG. 4A, it can be seen that the intensity of light leaving the solvent at a wavelength of $\lambda_{ref}$ may be given as:

$$I_{ref} = I_0 - I_{Wref}$$

where $I_0$ is the broadband incident light that is the same intensity for both wavelengths, and $I_{Wref}$ is the loss to water at $\lambda_{ref}$. From FIG. 4B, it can be seen that the intensity of light leaving the solvent at a wavelength of $\lambda_{sig}$ may be given as:

$$I_{sig} = I_0 - I_{Wsig} - I_{Clsig}$$

where $I_{Wsig}$ is the loss to water at $\lambda_{sig}$, $I_{Clsig}$ is the loss to chlorine at $\lambda_{sig}$.

The Beer-Lambert Law states:

$$\log_{10}(I_0/I) = \epsilon^* c_m{}^* L$$

where $\epsilon$ is the molar absortivity, $c_m$ is the molar concentration of solute, and L is the path length. Solving for $I_0/I$ in terms of the natural log (ln):

$$\log_{10}(e^1)*\log_e(I_0/I)=\epsilon*c_m*L$$

$$\log_{10}(e^1)=\log_{10}(2.718)=0.4343$$

$$\ln(I_0/I)=(\epsilon*c_m*L)/0.4343$$

$$I_0/I=e^{(\epsilon*cm*L)/0.4343}$$

The absorption coefficient $\alpha$ for a given solute may be given as:

$$\alpha=(\epsilon*c_m)/0.4343$$

For chlorine, $$\varepsilon \approx 8.374 \frac{\text{liters}}{\text{Moles}*\text{centimeters}} \text{ and } c_m = c * \frac{\text{Moles}}{17000 \text{ mg}},$$

where c is the concentration in parts per million (ppm) or $$\frac{\text{mg}}{\text{liter}}.$$

So for chlorine, the absorption coefficient $\alpha_{Cl}$ may be given as:

$$\alpha_{Cl} = \frac{8.374}{17000*0.4343}*c = 0.001134*c$$

From the Beer-Lambert Law, intensity losses can be written as:

$$I_{loss}=I_0*e^{(\alpha*L)}-I_0$$

Calculating the losses in FIG. 4A, then:

$$I_{ref}=I_0(2-e^{(\alpha(w1)*L)})$$

where the $\alpha(w1)$ is the absorption coefficient for water at $\lambda_{ref}$.

For the solute, using FIG. 4A:

$$I_{sig}=I_0(3-e^{(\alpha(Cl)*L)}-e^{(\alpha(w2)*L)})$$

where $\alpha(w2)$ is the absorption coefficient for water at $\lambda_{sig}$ and $\alpha(Cl)$ is the absorption coefficient for chlorine at $\lambda_{sig}$.

Taking the SNR as 10000:1 for the photodiodes, if 10000 is defined to be the maximum possible signal readable by a detector element (the saturation charge), and $I_{ref}$=10000, the measurement range may be represented as follows:

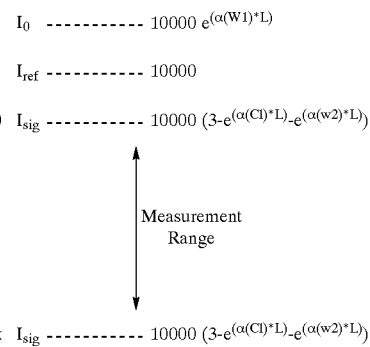

Thus, the measurement range is defined by the maximum signal intensity and the minimum signal intensity resolvable for a particular detector type. Taking $I_{sig}$=1 for a given path length L, then:

$$1=10000(3-e^{(\alpha(Cl)*L)}-e^{(\alpha(w2)*L)})$$

$$0.0001=3-e^{(\alpha(Cl)*L)}-e^{(\alpha(w2)*L)}$$

$$2.9999=e^{(\alpha(Cl)*L)}+e^{(\alpha(w2)*L)}$$

$$\ln(2.9999)=\alpha(Cl)*L\alpha(w2)*L$$

$$1.09858/L-\alpha(w2)=\alpha(Cl)$$

Inserting the equation for $\alpha(Cl)$, then:

$$1.09858/L-\alpha(w2)=0.001134*c_{max}$$

Solving for c:

$$c_{max}=1.09858/(L*0.001134)-\alpha(w2)/0.001134$$

$$c_{max}=968.8/L-\alpha(w2)*881.8$$

Thus, given a path length and absorption coefficient for the solvent at $\lambda_{sig}$, the max measurable concentration $c_{max}$ may be defined.

The smallest resolvable signal can be found by the following equation:

$$\text{min signal}=c_{max}/10000(2-e^{(\alpha(w2)*L)})$$

Applying these equations to the detection of chlorine:

$$L=20.32 \text{ cm}$$

$$\alpha(w2)=0.0036 \text{ cm}^{-1}$$

$$c_{max}=968.8/L-\alpha(w2)*881.8=50.9 \text{ ppm}$$

$$\text{min signal}=50.9/10000(2-e^{(\alpha(w2)*L)})=0.0055 \text{ ppm}$$

Thus, the range would be 0 to 50.9 ppm with increments of 0.0055 ppm.

According to exemplary embodiments, a non-intrusive solute concentration detection system has been developed that solves contamination problems and improves the accuracy of current sensors. The system may be used for direct insitu measurements of chlorine in water, reducing chemical use and lowering the overall cost of water treatment. The algorithm implemented on the system utilizes multi-point data. This eliminates error due to small fluctuations as seen with single point methods.

The system discussed herein is designed to further demonstrate that the photometric process used can overcome these difficulties and that it can accurately quantify active-chlorine concentrations in real time. By appropriately setting the optical path length of the chamber, it is possible to detect chlorine in the amounts of a few parts per million.

It should be understood that the foregoing description and accompanying drawings are by example only. A variety of modifications are envisioned that do not depart from the scope and spirit of the invention.

For example, although detection of chlorine in water has been described above, the system may be used to detect the concentration of any solute in a solution that has significant absorption in the UV, visable or near IR region.

The above description is intended by way of example only and is not intended to limit the present invention in any way.

What is claimed is:

1. A system for determining concentration of a solute in a solution, the system comprising:

an optical source for providing light in a predetermined wavelength range;

a chamber for containing the solute in the solution, the chamber having an input for receiving the light, an optical path length along which the light is transmitted through the solute and the solution in the chamber, and an output for outputting the light transmitted through the chamber;

a detector for receiving light transmitted along the optical path length of the chamber to the output of the chamber, wherein the optical path length of the chamber is selected to optimize sensitivity of the detector; and an analyzer for determining the concentration of the solute in the solution based on the light received by the detector, wherein the optical path length of the chamber is related to the sensitivity of the detector by the equations:

$$\text{min signal}=c_{max}/10000(2-e^{(\alpha(w2)\cdot L)})$$

$$c_{max}=968.8/L-\alpha(w2)*881.8$$

where min signal represents the minimum resolvable signal, $c_{max}$ represents the maximum detectable concentration, and L represents the optical path length of the chamber.

2. The system of claim 1, wherein the optical path length of the chamber is selected to provide an adequate intensity of light to the detector.

3. The system of claim 1, wherein the optical path length of the chamber is selected to provide an adequate resolution for the detector.

4. The system of claim 1, wherein the analyzer analyzes the spectral distribution of the received light and determines the concentration of the solute within the solution based on the spectral distribution.

5. The system of claim 1, wherein the detector includes an array of detectors.

6. The system of claim 1, wherein the detector determines based on a signature of the received light the concentration of the solute.

7. The system of claim 6, wherein the signature includes at least one peak absorption wavelength, and the detector includes a detector for each peak absorption wavelength.

8. The system of claim 1, wherein the detector includes a wavelength selective optics and photosensitive elements, and the analyzer analyzes the light detected by the photosensitive elements to determine the concentration of the solute in the solution.

9. The system of claim 8, wherein the wavelength selective optics include a diffraction grating.

10. The system of claim 8, wherein the wavelength selective optics include filters.

11. The system of claim 8, wherein the photosensitive elements include photosensitive diodes.

12. The system of claim 1, wherein the solute is chlorine, and the solution is chlorine in water.

13. The system of claim 1, wherein the chamber includes an input for the solution filling the chamber and output for outputting the solution.

14. The system of claim 13, wherein the flow of solution in and out of volume is controlled.

15. The system of claim 1, further comprising an analog and digital signal processing for comparing the received light of the detector with a reference signal.

16. The system of claim 15, wherein the reference signal is fed directly from the optical source to the detector.

17. The system of claim 15, wherein the analog and digital signal processing subtracts the reference signal from the detected signal to eliminate noise.

18. The system of claim 1, wherein the concentration of solute in the solution is determined in real time.

19. The system of claim 1, wherein the optical light source includes a controlled flashing light source.

20. The system of claim 1, wherein the detector sensitivity is in the parts per million (ppm) range.

21. A method for determining concentration of a solute in a solution, the method system comprising:

receiving light in a predetermined wavelength range from a light source at a chamber including the solute in the solution;

transmitting the received light along an optical path length of the chamber, through the solute in the solution in the chamber;

outputting the transmitted light from the chamber;

detecting the output light, wherein the optical path length of the chamber is selected to optimize sensitivity of the detection; and determining the concentration of the solute in the solution based on the light received by the detector, wherein the step of detecting is performed by wavelength selective optics and photosensitive elements, wherein the step of determining includes analyzing the light detected by the photosensitive elements to determine the concentration of the solute in the solution, wherein the photosensitive elements include photosensitive diodes, and wherein the optical path length of the chamber is related to the sensitivity of the detector by the equations:

$$\text{min signal}=c_{max}/10000(2-e^{(\alpha(w2)\cdot L)})$$

$$c_{max}=968.8/L-\alpha(w2)*881.8$$

where min signal represents the minimum resolvable signal, $c_{max}$ represents the maximum detectable concentration, and L represents the optical path length of the chamber.

22. The method of claim 21, wherein the optical path length of the chamber is selected to provide an adequate intensity of light to the detector.

23. The method of claim 21, wherein the optical path length of the chamber is selected to provide an adequate resolution for the detector.

24. The method of claim 21, wherein the step of determining includes analyzing the spectral distribution of the received light and determining the concentration of the solute within the solution based on the spectral distribution.

25. The method of claim 21, wherein the step of detecting is performed by an array of detectors.

26. The method of claim 21, wherein the step of determining included determines based on a signature of the received light the concentration of the solute.

27. The method of claim 26, wherein the signature includes at least one peak absorption wavelength, and the step of detecting includes detecting each peak absorption wavelength.

28. The method of claim 21, wherein the wavelength selective optics include a diffraction grating.

29. The method of claim 21, wherein the wavelength selective optics include filters.

30. The method of claim 21, wherein the solute is chlorine, and the solution includes chlorine in water.

31. The method of claim 21, wherein the chamber includes an input for the solution filling the chamber and output for outputting the solution.

32. The method of claim 31, wherein the flow of solution in and out of volume is controlled.

33. The method of claim 21, further comprising comparing the received light with a reference signal.

34. The method of claim 33, wherein the reference signal is fed directly from the optical source to the detector.

35. The method of claim 33, wherein the step of comparing comprises subtracting the reference signal from the detected signal to eliminate noise.

36. The method of claim 21, wherein the steps are performed in real time.

37. The method of claim 21, wherein the optical light source includes a controlled flashing light source.

38. The method of claim 21, wherein the detector sensitivity is in the parts per million (ppm) range.

39. An apparatus containing a solute in a solution, the apparatus comprising:

a volume for containing the solute in the solution;

an input for receiving light in a predetermined wavelength range from a light source;

an optical path length along which the light is transmitted through the solute in the solution in the chamber; and an output for outputting the light transmitted along the optical path length, wherein the output light is received at a detector and analyzed to determined the concentration of the solute in the solution, and the optical path length of the chamber is selected to optimize sensitivity of the detector, and wherein the optical path length of the chamber is related to the sensitivity of the detector by the equations:

$$\text{min signal} = c_{max}/10000(2 - e^{(\alpha(w2) \cdot L)})$$

$$c_{max} = 968.8/L - \alpha(w2) * 881.8$$

where min signal represents the minimum resolvable signal, $c_{max}$ represents the maximum detectable concentration, and L represents the optical path length of the chamber.

40. The apparatus of claim 39, wherein the optical path length is selected to provide an adequate intensity of light to the detector.

41. The apparatus of claim 39, wherein the optical path length is selected to provide an adequate resolution for the detector.

42. The apparatus of claim 39, wherein the spectral distribution of the output light is analyzed to determine the concentration of the solute within the solution based on the spectral distribution.

43. The apparatus of claim 39, wherein the output light is detected by an array of detectors.

44. The apparatus of claim 39, wherein the concentration of the solute is determined based on a signature of the received light the concentration of the solute.

45. The apparatus of claim 44, wherein the signature includes at least one peak absorption wavelength, and the output light is detected by a detector for each peak absorption wavelength.

46. The apparatus of claim 39, wherein the output light is detected by selective optics and photosensitive elements.

47. The apparatus of claim 46, wherein the wavelength selective optics include a diffraction grating.

48. The apparatus of claim 46, wherein the wavelength selective optics include filters.

49. The apparatus of claim 46, wherein the photosensitive elements include photosensitive diodes.

50. The apparatus of claim 39, wherein the solute is chlorine, and the solution includes chlorine in water.

51. The apparatus of claim 39, further comprising an input for the solution filling the volume and an output for outputting the solution.

52. The apparatus of claim 39, wherein the output light is compared with a reference signal.

53. The apparatus of claim 52, wherein the reference signal is fed directly from the optical source to the detector.

54. The apparatus of claim 53, wherein the reference signal is subtracted from the detected signal to eliminate noise.

55. The apparatus of claim 39, wherein the concentration of solute in the solution is determined in real time.

56. The apparatus of claim 39, wherein the input light is provide by a controlled flashing light source.

57. The apparatus of claim 51, wherein the flow of solution in and out of volume is controlled.

58. The apparatus of claim 39, wherein the detector sensitivity is in the parts per million (ppm) range.

* * * * *